Figure 1:
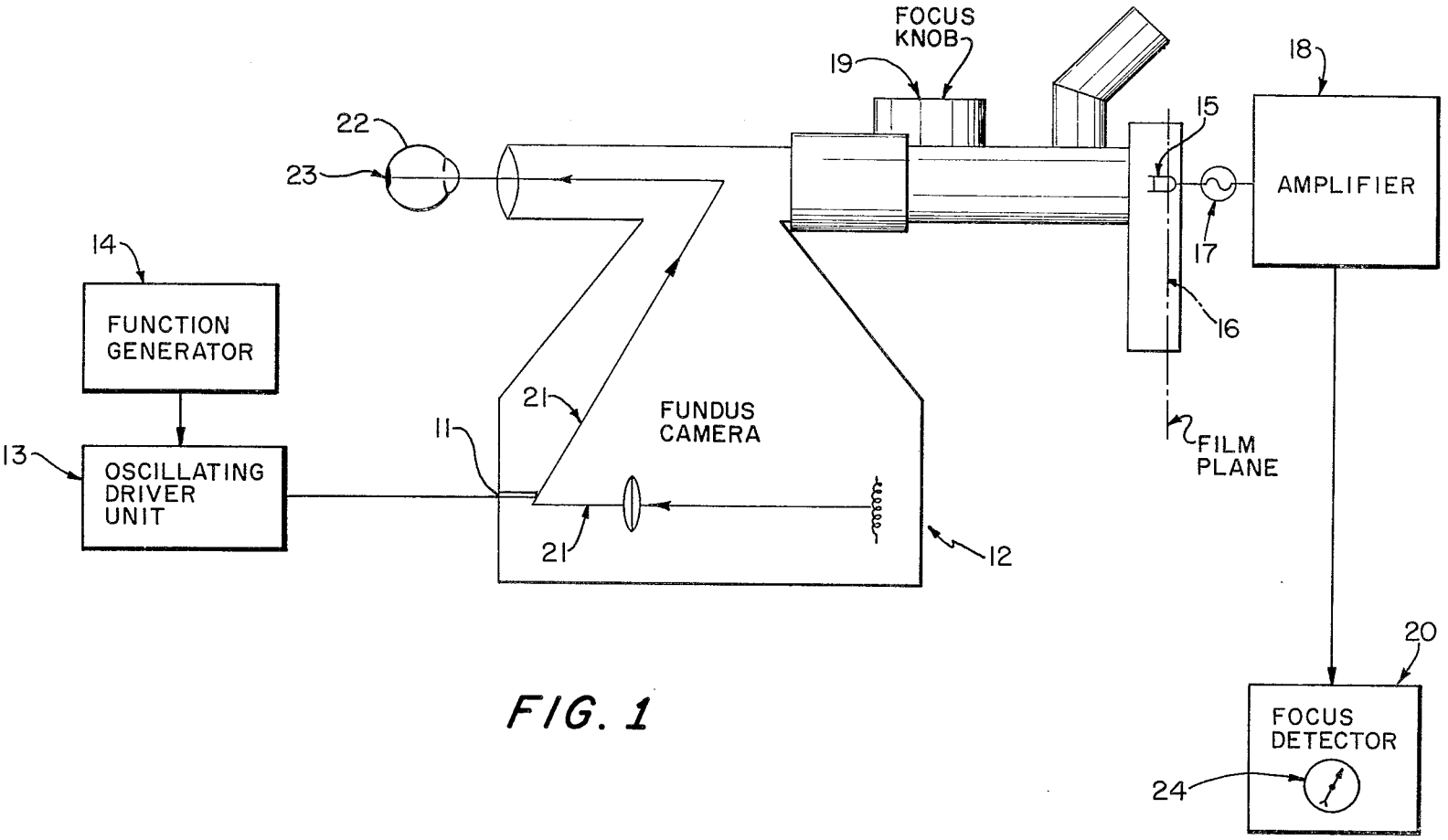
Figure 2:
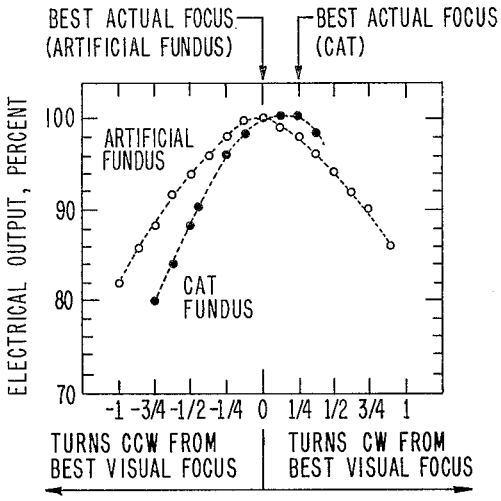
Figure 3:
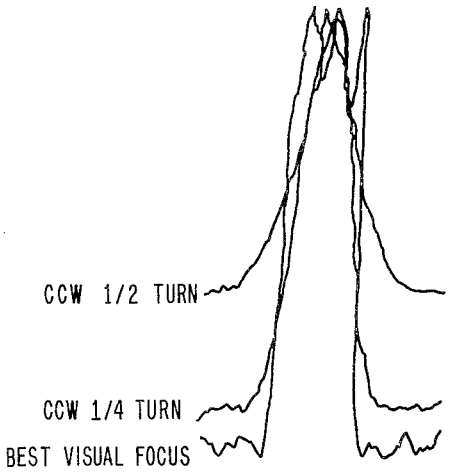
Figure 4:
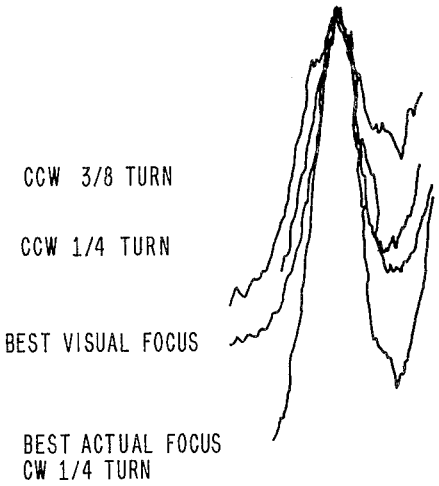

United States Defensive Publication [19] (H) [11] T958,011

Laing [43] May 3, 1977

[54] OBJECTIVE FOCUSING METHOD AND APPARATUS FOR FUNDUS PHOTOGRAPHY

[75] Inventor: Ronald A. Laing, Lexington, Mass.

[73] Assignee: The Trustees of Boston University, Boston, Mass.

[21] Appl. No.: 676,936

[22] Filed: Apr. 14, 1976

[51] Int. Cl.[2] ..... A61B 3/10

[52] U.S. Cl. ..... 351/7

[57] ABSTRACT

Apparatus and method for objectively focusing an instrument used for photographing the fundus of the eye such that consistent high resolution fundus photographs can be attained.

A narrow sharp oscillating needle 11 is focused onto the ocular fundus 22. The image 23 of the oscillating needle 11 moves past photodetector 15 located either at film plane 16 or at the plane of the crosshairs which are visible in the eyepiece or at any plane optically conjugate to the film plane. The spatial frequencies of image 23 are converted into a time-varying electrical signal at the output of photodetector 15. When image 23 of needle 11 is in best focus at film plane 16, its contrast is highest and the photodetector 15 will have a maximum alternating current output as indicated on focus detector 20.

5 Claims, 2 Sheets Drawing,

7 Pages Specification

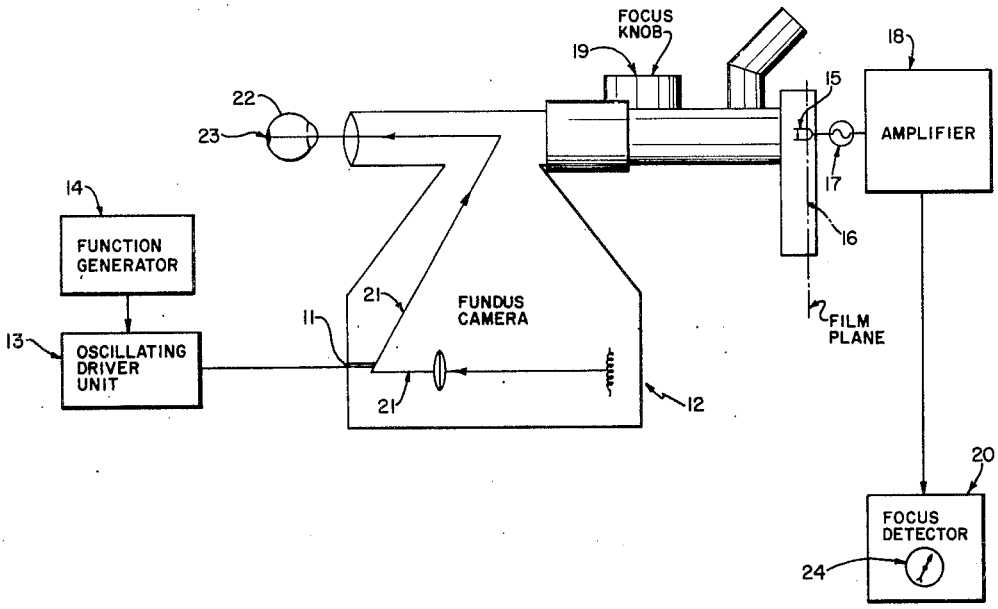

The file of this unexamined application may be inspected and copies thereof may be purchased (849 O.G. 1221, Apr. 9, 1968).